US00PP17517P3

(12) United States Plant Patent
Elsner

(10) Patent No.: US PP17,517 P3
(45) Date of Patent: Mar. 20, 2007

(54) *GERANIUM* PLANT NAMED 'TIKVIO'

(50) Latin Name: *Pelargonium×hortorum*
Varietal Denomination: Tikvio

(75) Inventor: Wilhelm Elsner, Dresden (DE)

(73) Assignee: Elsner pac Yungpflanzen, Dresden (DE)

( * ) Notice: Subject to any disclaimer, the term of this patent is extended or adjusted under 35 U.S.C. 154(b) by 1912 days.

(21) Appl. No.: 09/754,755

(22) Filed: Jan. 4, 2001

(65) Prior Publication Data

US 2002/0088038 P1 Jul. 4, 2002

(51) Int. Cl.
*A01H 5/00* (2006.01)

(52) U.S. Cl. ..... Plt./329; Plt./324

(58) Field of Classification Search ..... Plt./324, Plt./329
See application file for complete search history.

(56) References Cited

PUBLICATIONS

UPOV–ROM GTITM Computer Database, 2001/04, GTI Jouve Retrieval Software, citation for 'Tikvio'.*

* cited by examiner

*Primary Examiner*—Anne Marie Grunberg
*Assistant Examiner*—S. B. McCormick-Ewoldt
(74) *Attorney, Agent, or Firm*—The Webb Law Firm

(57) ABSTRACT

A new and distinct zonal *geranium* plant with bright violet colored flowers above medium green foliage with distinct zonation. The plant may be grown in a pillar form when supported.

1 Drawing Sheet

Classification: *Pelargonium×hortorum* (zonal *geranium*). Varietal denomination: 'Tikvio'.

BACKGROUND OF THE INVENTION

The present invention comprises a new and distinct cultivar of *Pelargonium×hortorum* known by the commercial names 'pac$^R$ Antik Violet, Tikvio$^{(s)}$ and pac$^R$ Pillar Violet, Tikvio$^{(s)}$ (Breeder No. P-6138). The new variety was discovered in 1996 in a selected breeding program in Dresden, Germany. The new variety is a selection a population of seedlings resulting from breeding and crossing of diploid group 95K-37. The new variety is vigorous with long internodes similar to the plants of its heritage but differs in its bright violet flower color. The new variety was first asexually reproduced by cuttings in Dresden, Germany. The new variety has been trial and field tested at Connellsville and has been found to retain its distinctive characteristics and remain true to type through successive propagations.

The new variety is comparable to 'Tikorg' (U.S. patent application Ser. No. 09/753,976) but has less branching, violet flower color instead of orange and is hairier.

The cultivar, when grown in a glass greenhouse in Connellsville, Pa. using natural light and temperatures of 60° F. night and 68° F. day, has a response time of six weeks from a rooted cutting to flowering in a 2 inch pot and a response time of 10–12 weeks to a saleable pillar product. The response time was determined on plants grown in soilless media employing constant fertilizer 200–250 parts per million of nitrogen and potassium in full light.

DESCRIPTION OF THE DRAWINGS

The accompanying photographic drawing illustrates the new variety, with the color being as nearly true as is possible with color illustrations of this type.

DESCRIPTION OF THE PLANT

The following detailed description sets forth the characteristics of the new cultivar. The data which defines these characteristics were collected by asexual reproductions carried out in Connellsville, Pa. The color readings were taken indoors under 200–220 foot candles of fluorescent cool white light. Color references are primarily to The R.H.S. Colour Chart of The Royal Horticultural Society of London, 1995 edition.

PLANT

Form: Tall bush.
Height: 24–36 inches.
Growth: Free branching, lateral to upright growth.
Strength: If grown in pillar form, support required.
Foliage: Stalked leaf.
Rooting time: 14–21 days depending on conditions.
Leaves:
- *Size.*—Length: 5.5–7.0 cm. Width: 7.5–8.0 cm.
- *Shape.*—Reniform; cordate base.
- *Margin.*—Crenate.
- *Texture.*—Pubescent.
- *Color.*—Upper surface: Green Group 137A. Lower surface: Green Group 137C. Zone: Greyed-Purple Group 187A.
- *Ribs and veins.*—Venation: Palmate. Color: Yellow-Green Group 144D.

Petioles:
- *Color.*—Yellow-Green Group 144A with some shading of Greyed-Purple Group 187B.
- *Length.*—6.0–7.0 cm.
- *Diameter.*—4 mm.

Stem:
- *Diameter.*—8 mm.

THE BUD

Shape when just beginning to show color:
*Overall.*—Semi-spherical.
*Individual bud.*—Elongated elliptical (oval).
Size when just beginning to show color:
*Overall.*—4.0–4.5 cm across.
*Individual bud.*—0.5–0.7 cm wide; 1.2–1.5 cm long.
Number of buds per cluster: 15–20.

INFLORESCENCE

Blooming habit: Continuous flowering.
*Size.*—11.5–12.5 cm across.
*Borne.*—Flower on umbel; umbel on pedicel; pedicel on peduncle.
Flowers:
*Form.*—Slightly cupped, some petals overlap.
*Number of flowers per umbel.*—20–25.
*Size.*—Diameter: 4.5–4.7 cm. Depth: 1.–1.5 cm.
*Petals.*—Color: Upper surface: Red-Purple Group 66A, some petals have slight outer edge rim of Red-Purple Group 57A. Toward the base of petal the color shades to Red Group 50A. On the upper two petals there is an area of Red Group 52A shading to small areas of Red Group 50A. Some petals have darker veining of Red Group 53B. Lower surface: Wide color range including: Red-Purple Groups 58B and 58C, and Red Group 50B. Some petals have dark veining that shows through. Shape: Round at top with a narrower bottom. Size: Length: 2.4–2.6 cm. Width: 1.8–2.4 cm. Margin: Bicrenate. Number per flower: 5.
*Sepals.*—Color: Green Group 138A. Size: 8 mm long; 5 mm wide. Number per flower: 5.
Texture and appearance: Smooth, highly reflective.
Tonality from a distance: Striking magenta flowers with tones of deep red, and violet varying in amount and intensity.
Petaloids: None.

Pedicel:
*Length.*—4.0–4.3 cm.
*Diameter.*—1.0–1.5 mm.
*Color.*—Greyed-Purple Group 184A with Yellow-Green Group 144D at base.
Peduncle:
*Length.*—18–20 cm.
*Diameter.*—4–5 mm.
*Color.*—Yellow-Green Group 144A with shading of Greyed-Purple Group 187B.
Disease/pest resistance: No unusual susceptibility to diseases or pests has been noted to date.

REPRODUCTIVE ORGANS

*Filaments.*—Length: 0.4–0.5 cm. Color: Yellow-Green Group 145C.
*Pollen.*—Orange Group 24B.
Pistils:
*Number.*—One.
*Length.*—0.7 cm.
*Stigma.*—Number: One. Color: Yellow-Green Group 150D.
*Style.*—Length: 0.2–0.3 cm. Color: Yellow-Green Group 150D.
Ovaries:
*Length.*—0.5 cm.
*Width.*—0.3 cm.
*Color.*—Green Group 142B.
Fruit: None observed.

GENERAL CHARACTERISTICS

1. 'Tikvio' is a very vigorous grower which allows it to be trained as a pillar.

2. 'Tikvio' is very floriferous and unique to the *geranium* industry.

3. Tolerant to drought and some heat; not winter hardy.

I claim:

1. A new and distinct variety of *geranium* plant substantially as shown and described.

* * * * *

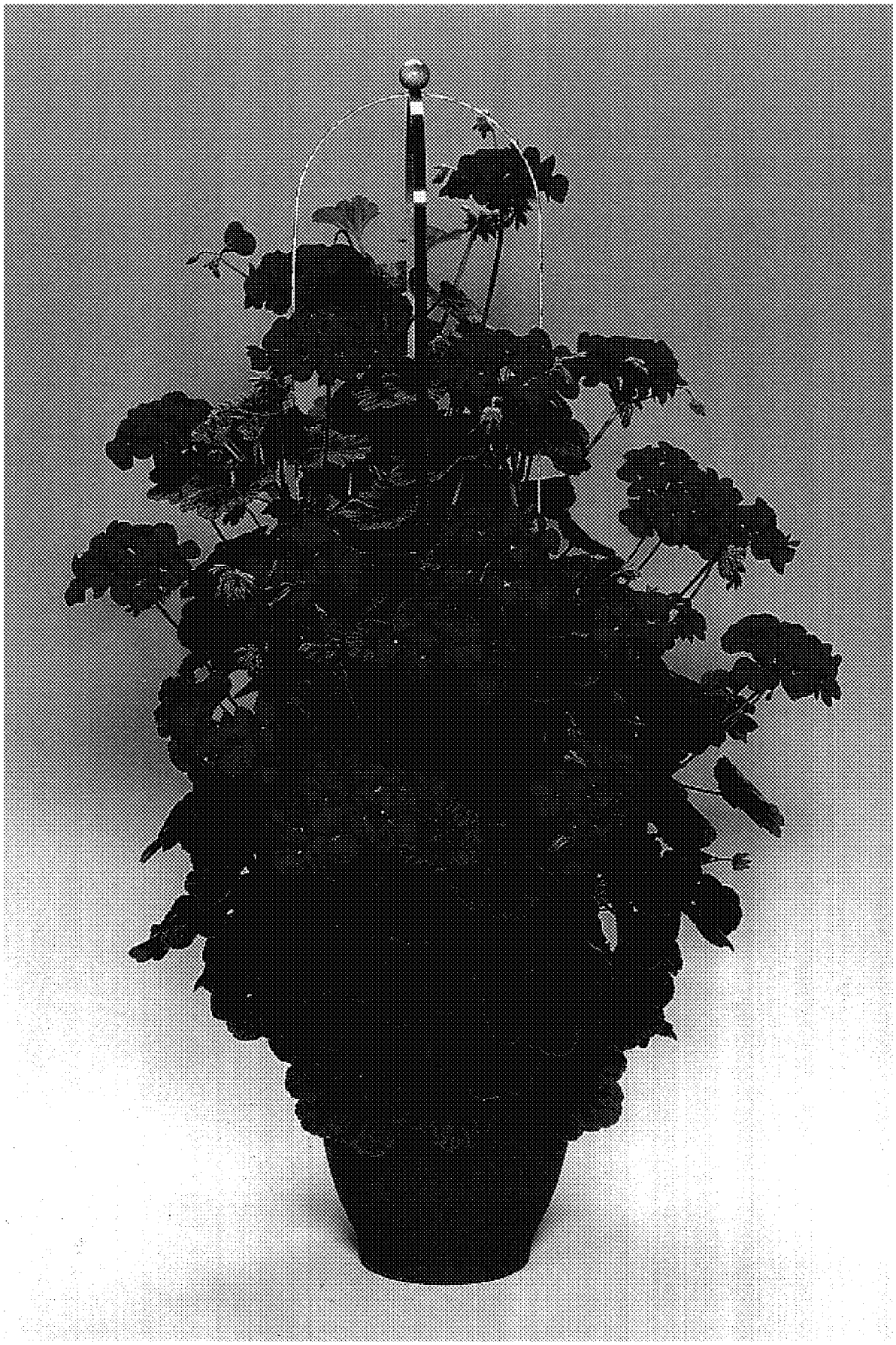

UNITED STATES PATENT AND TRADEMARK OFFICE

CERTIFICATE OF CORRECTION

PATENT NO. : PP 17,517 P3
APPLICATION NO. : 09/754755
DATED : March 20, 2007
INVENTOR(S) : Elsner It is certified that error appears in the above-identified patent and that said Letters Patent is hereby corrected as shown below:

(1) Title of the Patent, See Item (73) Assignee, "Elsner pac Yungpflanzen" should read -- Elsner pac Jungpflanzen --

(2) Column 2, Line 4, "new cultivar." Should read -- new cultivar at 9 months. --

(3) Column 2, Line 38, after "Stem:" and before "Diameter: 8 mm.", insert the following:
-- Color: Green Group 137C.
Internode Length: 2.5—4.5 cm. --

(4) Column 3, Under "Petals:" Line 8, after "Wide color range including:", insert the following:
-- Red-Purple Group 64C, Red-Purple Group 63B, Red-Purple Group 61C, --

(5) Column 4, Line 1, after "Reproductive Organs", insert the following:
-- Stamens:
Anthers: 0.2—0.25 cm --

Signed and Sealed this

Third Day of July, 2007

JON W. DUDAS
*Director of the United States Patent and Trademark Office*